United States Patent [19]

Cipar

[11] Patent Number: 5,434,342

[45] Date of Patent: Jul. 18, 1995

[54] POTATO CULTIVAR

[76] Inventor: Martin S. Cipar, 4057 Keewatin Trail, Verona, Wis. 53593

[21] Appl. No.: 44,214

[22] Filed: Apr. 30, 1987

[51] Int. Cl.$^6$ .......................... A01H 5/00; C12N 5/00
[52] U.S. Cl. .......................... 800/200; 800/DIG. 42; 435/240.4
[58] Field of Search .................. 800/1, 200, DIG. 42; 47/58; 435/240.4

[56] References Cited

PUBLICATIONS

Poehlman, J. 1959, pp. 2,4 and 53–64, In: Breeding field crops, Holt, Rinehart & Winston: New York.
Allard, R. 1960, pp. 35–36 In: Principles of plant breeding, John Wiley & Sons: New York.
Briggs et al. 1967, Introduction to plant breeding, Reinhold Publishing: New York, p. 46.
"The Marygold Potato", R. A. Jehle and F. J. Stevenson, *The American Potato Journal*, 1949, pp. 25–32.
Desborough and Peloquin, *Amer. Potato J.* 45:220–229 (1968).
Desborough and Peloquin, *Phytochemistry* 6:989–994 (1967).
Desborough and Peloquin, *Theoretical and Applied Genetics* 39:43–47 (1969).
Desborough and Peloquin, *Phytochemistry* 5:727–733 (1966).
*The Compendium of Licensed Varieties* published by the Canadian Department of Agriculture.
Desborough and Peloquin, *Phytochemistry* 5:727–733 (1966).
*The Compendium of Licensed Varieties* published by the Canadian Department of Agriculture.
Desborough and Peloquin, *Amer. Potato J.* 45:220–229 (1968).
Desborough and Peloquin, *Phytochemistry* 6:989–994 (1967).
Desborough and Peloquin, *Theoretical and Applied Genetics* 39:43–47 (1969).
Dearborn, C. 1979. Amer. Pat. J. 56(8):373–378.
Reeves et al. 1980. Amer. Pat. J. 57(9):429–433.

*Primary Examiner*—David T. Fox

[57] ABSTRACT

A novel potato cultivar of the genus and species *Solanum tuberosum*, Group Tuberosum, having moderately green foliage, vigorous vine growth and white flowers, having tubers characterized by a white flesh color, white tuber skin color, a relatively high specific gravity, a somewhat flattish round to blocky-oval shape, and having a characteristic protein electrophoretic "fingerprint" pattern.

5 Claims, 4 Drawing Sheets

FL 1625

POTATO CULTIVAR

BACKGROUND OF THE INVENTION

The present invention relates to a novel potato cultivar and to tubers produced by that potato cultivar.

The potato is one of the world's most important food crops. Potatoes are currently grown commercially in nearly every state of the United States. Annual potato production exceeds 18 million tons in the United States and 300 million tons worldwide. The popularity of the potato stems mainly from its versatility and nutritional value. Potatoes can be used fresh, frozen or dried, or can be processed into flour, starch or alcohol. They contain complex carbohydrates and are rich in calcium, niacin and vitamin C.

To keep the potato industry growing to meet the needs of the consuming public, substantial research and development efforts are devoted to the modernization of planting and harvesting of fields and processing of potatoes, and to the development of economically advantageous potato varieties. Through cross-breeding of potatoes, researchers hope to obtain potatoes with the desirable characteristics of good processability, high solids content, high yield, resistance to diseases and pests and adaptability to various growing areas and conditions.

The acreage planted in potatoes has declined steadily for many years, and this decline, coupled with increasing consumption, must be offset by higher useable yields. In some areas, diseases and pests damage crops despite the use of herbicides and pesticides. The problem of the golden nematode in the United States, presently endemic to portions of New York state, is one example of the destruction to susceptible potato varieties. Potato varieties with high yields, disease resistance, and adaptability to new environments can eliminate many problems for the potato grower and provide more plentiful and economical products to the consumers.

For the potato chip processing industry, potatoes having high solids content, good shipping qualities and good finished chip color can increase production volumes and efficiencies and product acceptability. Potato varieties which yield low-solids tubers result in unnecessary energy usage during the frying process. Moreover, as solids content increases, the oil content of fried products decreases, which is a favorable improvement. Potato varieties in the warm southern tier of states are most in need of solids improvement overall, while those varieties grown and stored in the colder northern tier of states are most in need of the ability to recondition after cool or cold storage to increase their value for use in the potato chip industry. Reconditioning is necessary to elevate the temperature of the potatoes after cold storage and before further processing.

The research leading to potato varieties which combine the advantageous characteristics referred to above is largely empirical. This research requires large investments of time, manpower, and money. The development of a potato cultivar can often take up to eight years or more from greenhouse to commercial usage. Breeding begins with careful selection of superior parents to incorporate the most important characteristics into the progeny. Since all desired traits usually do not appear with just one cross, breeding must be cumulative.

Present breeding techniques begin with the controlled pollination of parental clones. Typically, pollen is collected in gelatin capsules for later use in pollinating the female parents. Hybrid seeds are sown in greenhouses, and tubers are harvested and retained from thousands of individual seedlings. The next year the tubers are planted in the field, where extreme caution is exercised to avoid the spread of viruses and diseases. From this first-year seedling crop, several "seed" tubers from each hybrid individual which survived the selection process are retained for the next year's planting. After the second year, samples are taken for density measurements and fry tests to determine the suitability of the tubers for commercial usage. Plants which have survived the selection process to this point are then planted at an expanded volume the third year for a more comprehensive series of fry tests and density determinations. At the fourth-year stage of development, surviving selections are subjected to field trials in several states to determine their adaptability to different growing conditions. Eventually, the varieties having superior qualities are transferred to other farms and the seed increased to commercial scale. Generally, by this time, a full eight years of planting, harvesting and testing have been invested in attempting to develop the new and improved potato cultivars.

Heretofore, significant progress has been made in the development of disease-resistant, high-yield potato cultivars. U.S. patent application Ser. No. 827,373 describes a novel, disease-resistant, high-yield potato cultivar, FL1553. There is a continuing need to develop potato cultivars which combine the properties of disease resistance, resistance to pests, particularly the golden nematode, and good processability for manufacturers of potato chips and other potato products.

SUMMARY OF THE INVENTION

In accordance with the present invention, a novel potato cultivar of the genus and species, *Solanum tuberosum*, Group Tuberosum is disclosed. This cultivar has moderately green foliage, vigorous vine growth and white flowers and produces tubers which are characterized by a white color, white tuber skin color, a good specific gravity, and a somewhat flattish round to blocky oval shape. The tubers have a characteristic protein electrophoretic pattern, as hereinafter described.

BRIEF DESCRIPTION OF THE DRAWINGS

The file of this patent contains at least one drawing executed in color to meet the requirements of 35 U.S.C. § 112. Copies of this patent with color drawings will be provided by the Patent and Trademark Office upon request and payment of the necessary fee.

DETAILED DESCRIPTION OF THE INVENTION

A novel potato cultivar of the present invention, which has been designated FL1625, has been obtained by selectively cross breeding parental clones through several generations. The immediate parents of FL1625 were cultivars designated RD208-1-1 (♀) and RD86-2-5 (♂), which were proprietary cultivars developed earlier during research for new varieties of potatoes. The pedigree of FL1625 includes such commercial, named cultivars as Monona, Katahdin, Delta Gold and Kennebec, as well as their progenitors. These parent strains were selected for their properties of resistance to diseases or pests, good yield, solids content, chipping quality and physical appearance among other traits. In particular, the parent strains were known as manifesting some resistance to late blight, while their progenitors were known to possess a late blight race specific gene or genes conferring a hypersensitive form of resistance to the fungal pathogen. The parent strains were also known to manifest good solids and yield.

Figure 2:
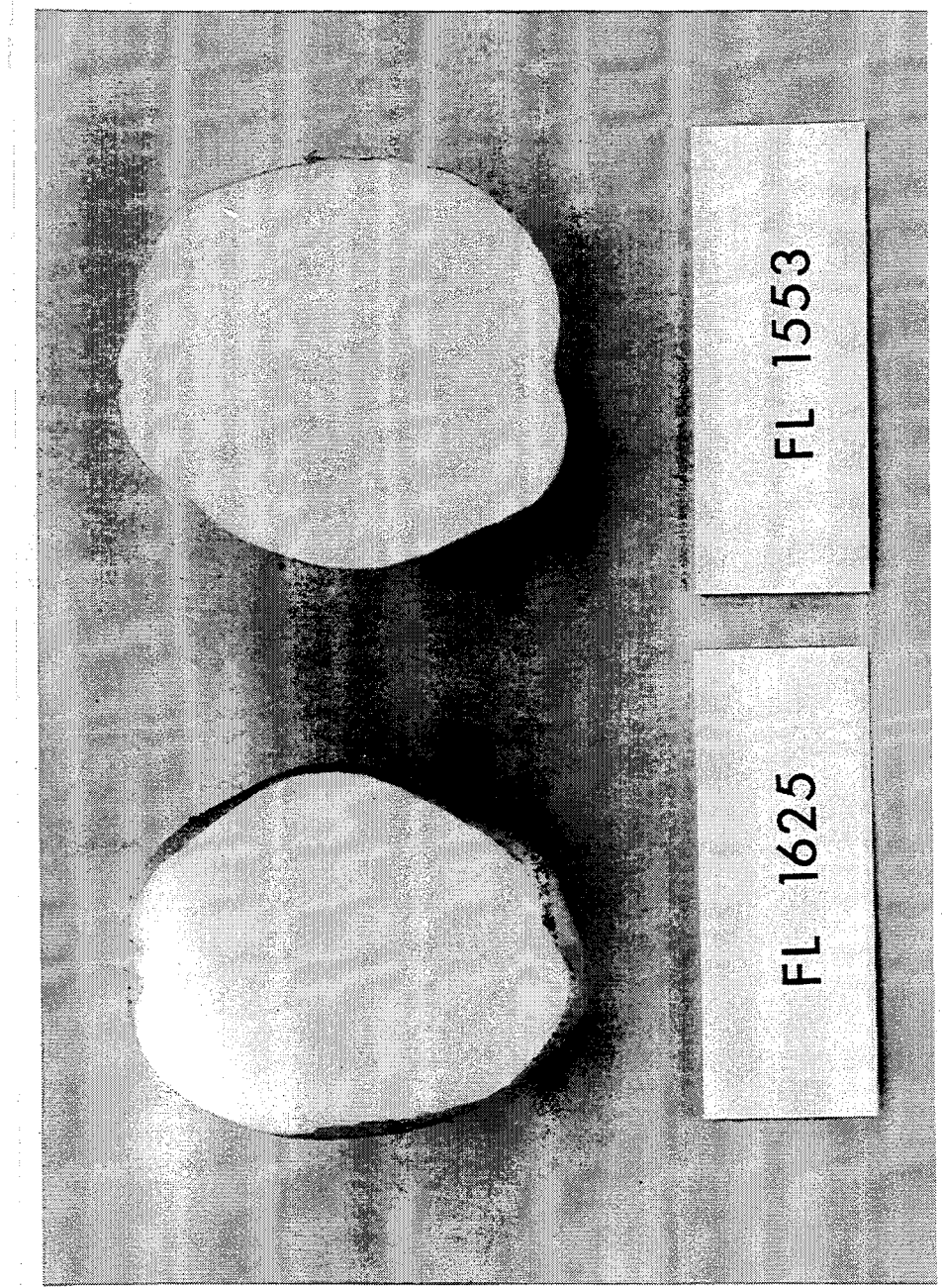
FIG. 2 is a photograph of cut tubers from potato cultivars FL1553 and FL1625.
Figure 3:
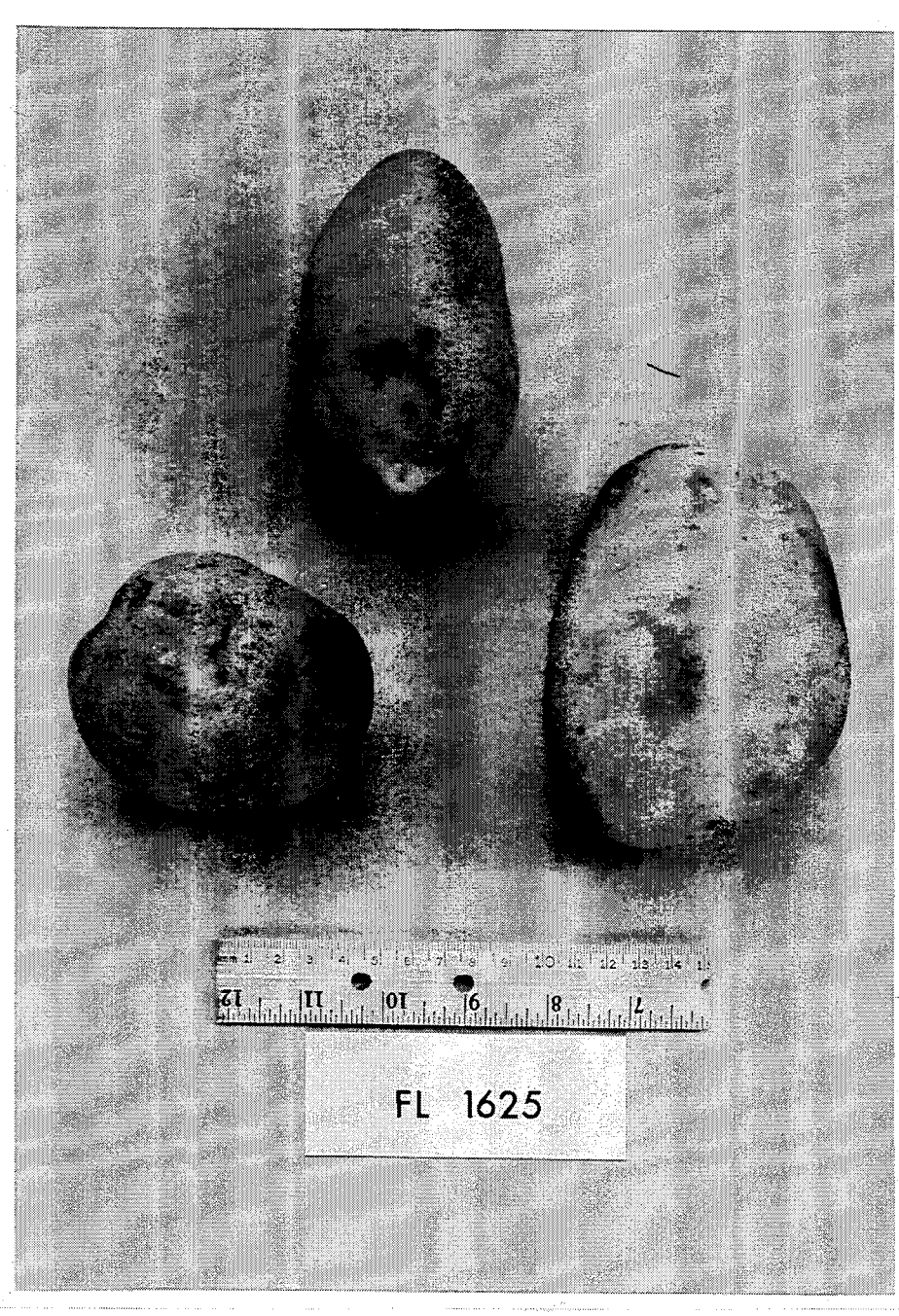
FIG. 3 is a photograph of whole tubers from potato cultivar FL1625.
Figure 4:
FIG. 4 is a photograph of the sprout morphology of potato cultivar FL1625.

The novel potato cultivar of this invention is of the genus and species *Solanum tuberosum,* Group Tuberosum. FIG. 2 shows the white color of the flesh of the tuber from FL1625 as distinguished from the yellow flesh of the earlier developed FL1553. The whole tubers from potato cultivar FL1625 are shown in FIG. 3 and have a white skin color and white eyes. The foliage of FL1625 is moderately green and exhibits vigorous vine growth. FIG. 4 shows the sprout morphology of FL1625 which can be quite distinctive. See, *Compendium of Licensed Varieties,* Agriculture Canada. The flowers are white. The mean length to width index of terminal and lateral leaflets on the plants, as calculated from measurements of 118 compound leaves, was (length÷width) 59.02 for lateral leaflets and 62.60 for terminal leaflets. FL1625 is noted for its good vine vigor and tuber yield where adapted.

The tubers produced by this cultivar are well-suited for the production of potato chips. A characteristic feature of the tubers is their comparatively good specific gravity relative to the standard commercial variety in a production area. The specific gravity generally ranges from about 1.062 to about 1.107; however, it will be appreciated that specific gravities can vary substantially depending upon growing conditions and areas. Higher specific gravities are advantageous for chipping and other frying applications, as they reduce the total energy and time required for the frying operation. The high solids content of these tubers also reduces the frying oil content of resulting finished products, a beneficial property with respect to calorie content, shelf life, and other features. High tuber solids are an advantage for chipping potatoes grown in the southern tier of states especially. The tubers of FL1625 are a high solids variety with very good chip processing characteristics, both directly from the field and from cool or cold storage. These tubers result in chips with good color and few defects.

In addition to the specific gravity of the tubers of this invention, they also have an advantageous shape for commercial operations. The tubers are relatively smooth skinned. They generally lack knobs and other protuberances, as well as deep ridges or convolutions. Accordingly, they are amenable to efficient washing and peeling operations using large-scale automated equipment. Such shapes produce a high quality product with a minimal amount of waste. The tubers are generally flattish oval in shape but may vary from a round to a blocky-oval shape and have a size which is suited to the manufacture of potato chips. In general, these tubers have a mean length of 10.069 centimeters (range: 8.57–12.06 centimeters); a mean width of 8.328 centimeters (range: 7.30–9.52 centimeters) and a mean thickness of 6.414 centimeters (range: 5.39–8.25 centimeters) based upon a 100-tuber sample. The mean weight was 297.99 grams (range: 234.4–379.4 grams). Of course, the size of the tubers can vary over a relatively wide range depending upon growing conditions and locations. The slightly flattened shape of the tubers is advantageous, because it facilitates alignment in the slicing apparatus. FL1625 has the ability to process off the field as well as reconditioned from cold storage.

Other advantageous properties of the plants of the present invention include competitive yield, where adapted and the ability to grow and yield well under dryland cultural conditions. FL1625 is moderately resistant to common scab disease and may be less susceptible to the disease than other cultivars where environmental conditions favor the disease, such as where soil pH is relatively high or where dryland cultural conditions prevail.

FL1625 can develop an abiotic defect called "hollow heart", especially when tuber size gets too large, and is not known to be resistant to common potato viruses.

In addition to the morphological characteristics and disease resistance described above, the plants of this invention are characterized by their protein "fingerprint" patterns. The protein fingerprint is determined by separating tuber proteins on an electrophoretic gel under certain defined conditions. The pattern of the proteins, attributable to their differential mobilities on the electrophoretic gel, have been found to be characteristic of the particular plant involved. This pattern has thus been termed a "fingerprint." The protein fingerprinting technique has been used by different investigators to differentiate large numbers of potato varieties. See, Desborough, S. and Peloquin, S. J., *American Potato Journal,* 45, 220–229 (1968) and Desborough, S. and Peloquin, S. J., *Theoretical and Applied Genetics,* 39, 43–47 (1969). These techniques generally involve extracting proteins from the tuber and applying the extract to an electrophoretic gel (e.g., polyacrylamide). The proteins are separated electrophoretically, and peroxidase and esterase enzyme systems as well as other soluble proteins are visualized by staining techniques and the application of enzyme substrates. Electrophoretic patterns of proteins solubilized with sodium dodecyl sulfate (SDS) and esterases have been found particularly valuable in characterizing potato cultivars. The protein fingerprinting technique and patterns are described more fully in the drawings and in the examples which follow.

Potato cultivar FL1625 has been deposited with American Type Culture Collection 12301 Parklawn Dr., Rockville, Md. 20852 and given Accession Number 40316. This depository is independently maintaining the cultivar in sterile tissue culture using conventional micropropagation techniques. Plants which are genetically identical to the original deposit can be obtained by growing these tissue cultures and transplanting into greenhouses and ultimately fields.

Thus, according to the present invention a novel potato cultivar having desirable characteristics of disease resistance, yield, color, specific gravity, adaptability to varying cultural conditions, and processability has been disclosed. The invention is further illustrated by the following examples which are not intended to be limiting.

EXAMPLE I

This example describes the determination of electrophoretic fingerprint patterns for proteins extracted from tubers of FL1625.

MATERIALS

Basic Extraction Buffer 2 g tris (hydroxymethyl)aminomethane (TRIS)
6.6 g glycine
0.5 g sodium metabisulfite
q.s. distilled water to 250 ml.
pH 8.3

Acidic Extraction Buffer 31.2 g $\beta$-alanine
8 ml glacial acetic acid
q.s. distilled $H_2O$ to 100 ml $H_2O$

SDS Extraction Buffer 0.30 g TRIS (as pH 6.8 aq. solution)
10 g glycerol
5 g mercaptoethanol
30 ml. 10% sodium dodecylsulfate (SDS)
q.s. distilled water to 100 ml.

Basic Acrylamide Gels

Stock Solutions:
  Stock A
    48 ml 1N HCl
    36.3 g TRIS
    0.46 ml N,N,N',N''-tetramethylenediamine (TEMED)
    q.s. distilled $H_2O$ to 100 ml.
    pH 8.8–9
  Stock B
    25.6 ml 1M $H_3PO_4$
    0.46 ml TEMED
    5.7 g TRIS
    q.s. distilled $H_2O$ to 100 ml.
    pH 6.9
  Stock C
    30.0 g acrylamide
    0.8 g N,N'-methylenebisacrylamide
    q.s. distilled $H_2O$ to 100 ml.
  Stock D
    10.0 g acrylamide
    0.5 g N,N'-methylenebisacrylamide
    q.s. distilled $H_2O$ to 100 ml.
  Stock E
    riboflavin 4 mg/100 ml.
  Stock G
    ammonium persulfate
    0.14 g/100 ml
Basic Reservoir Buffer
  28.8 g glycine
  6 g TRIS
  q.s. distilled $H_2O$ to 1 liter
  pH 8.3

7½% running gels are prepared by combining the following:
  3.0 ml Stock A
  6.0 ml Stock C
  3.0 ml $H_2O$
  12.0 ml Stock G
Stacking gels are prepared by combining the following:
  1.0 ml Stock B
  1.5 ml Stock D
  0.5 ml Stock E
  1.75 ml distilled $H_2O$

Acidic Acrlyamide Gels

Stock Solutions
  Stock A
    48 ml 1N KOH
    17.2 ml glacial acetic acid
    4.0 ml TEMED
    q.s. distilled $H_2O$ to 100 ml
    pH 4.3
  Stock B
    48 ml 1N KOH
    2.87 ml glacial acetic acid
    0.46 TEMED
    q.s. distilled $H_2O$ to 100 ml
    pH 6.7
  Stock C
    30 g. acrylamide
    0.8 g bis (acrylamide)
    q.s. distilled $H_2O$ to 100 ml
  Stock D
    10 g. acrylamide
    2.5 g. bis (acrylamide)
    q.s. distilled $H_2O$ to 100 ml
  Stock E
    2 mg riboflavin
    q.s. distilled $H_2O$ to 50 ml
  Stock G
    0.14 g ammonium persulfate
    q.s. distilled $H_{20}$ to 100 ml
Acidic Reservoir Buffer
  31.1 2g. $\beta$-alanine
  8 ml glacial acetic acid
  q.s. distilled $H_2O$ to 1 liter
  pH 4.0
Running gels are prepared by combining the following:
  3.0 ml Stock A
  6.0 ml Stock C
  3.0 ml distilled $H_2O$
  12.0 ml Stock G
Stacking gels are prepared by combining the following:
  1.0 ml Stock B
  1.5 ml Stock D
  0.5 ml Stock E
  1.75 ml distilled $H_2O$

SDS Acrylamide Gels

Stock Solutions
Running Gel Buffer
  1.5M TRIS-HCl, pH 8.8
Stacking Gel Buffer
  0.5M TRIS, pH 6.8
12% running gels are prepared by combining the following:

2.4 ml distilled
4.0 ml Stock C (from Basic Acrylamide Gels)
3.5 ml running gel buffer
100 λ 10% SDS
20 λ 10% ammonium persulfate
5 λ TEMED
to total of 10 ml 10% running gels are prepared by combining the following:
4.0 ml distilled $H_2O$
3.3 ml Stock C (from Basic Acrylamide Gels)
2.5 ml running gel buffer
100 λ 10% SDS
50 λ 10% ammonium persulfate
5 λ TEMED
to total of 10 ml 12.5% running gels are prepared by combining the following:
3.3 distilled $H_2O$
4.2 ml Stock C (from Basic Acrylamide Gels)
2.4 ml running get buffer
100 λ 10% SDS
10 λ TEMED
75 λ 10% ammonium persulfate
to total of 10 ml Stacking gels for each of the running gels are prepared by combining the following:
3.1 ml distilled $H_2O$
0.5 ml Stock C (from Basic Acrylamide Gels)
1.75 ml stacking gel buffer
50 λ 10% SDS
50 λ 10% ammomium persulfate
5 λ TEMED
to total of 10 ml Reservoir buffer for SDS-Acrylamide gels is prepared by combining the following:
200 ml Basic Reservoir Buffer
20 ml 10% SDS
q.s. distilled $H_2O$ to 2 liters Coomassie Blue Dye Staining Solution 454 ml 50% methanol
46 ml glacial acetic acid
0.125 g Coomassie Blue Dye R-250 (Pierce Chemical Co.)
(Solution filtered through filter paper before use.)

Clearing Solution 45 4 ml 50% methanol
46 ml glacial acetic acid

Esterase Staining Solution 2.5 ml of 1% w/v α-naphthylacetate in acetone
50 mg fast blue RR salt
q.s. 0.01M pH 7 phosphate buffer to 50 ml.

Aniline Blue Black Staining Solution

1% solution of aniline blue black
7.5% glacial acetic acid

PROCEDURE

Five grams of fresh tuber from FL1625 were cut into small cubes, and these cubes were soaked in 0.7% sodium hydrosulfite in the cold for at least 30 minutes. The cubes were rinsed thoroughly with distilled water and 1 ml of Basic Extraction Buffer or Acidic Extraction Buffer was added to the cubes. This mixture was then ground to a fine slurry. The slurry was centrifuged at 16,000×g for 30 minutes and the supernatant used for electrophoresis in the 7½% basic acrylamide gels or the acidic acrylamide gels. A portion of the supernatant was diluted 1:1 with SDS Extraction Buffer and heated to boiling and this solution was used for electrophoresis in 10% or 12.5% SDS gels. Ten percent gels are used to separate proteins with higher molecule weight. The percentage represents the concentration of acrylamide and may be changed to increase the clarity of the protein bands. When comparing gels for identification purposes, the same concentrations should be compared.

Slab gels were prepared in the conventional manner, using the SDS Acrylamide running and stacking gel compositions described above. Running gels were poured to within ¾ inch of the top of the gel and polymerized, and the remaining space was filled with stacking gel. Tuber protein extracts in SDS Extraction Buffer (25 λ samples) were applied to the SDS Acrylamide Gels (10% and 12.5%), respectively. The gels were placed in conventional apparatus, and the reservoirs filled with the appropriate reservoir buffers as described above. Current was applied (60 m Amperes) and electrophoresis was run in the conventional manner. After completion of electrophoresis (as evidenced by the location of a tracking dye), the gels were removed from the apparatus and the stacking gels removed.

Tube gels were prepared in the conventional manner to obtain basic acrylamide, acidic acrylamide, and basic gels total protein electrophoretic fingerprints of FL1625. The same procedure was followed as above using the materials listed for the Basic Acrylamide Gels and the Acidic Acrylamide Gels, except utilizing a the gel procedure rather than a slab gel procedure. The tube gels for checking basic gels total protein were set up with the same materials as for the other Basic Acrylamide gels except these tubes were stained for protein rather than esterases as with the Basic Acrylamide Gels (described below).

The protein bands were visualized as follows:

Soluble Proteins

The 10% and 12.5% SDS Acrylamide Gels were placed in a disk and covered with Coomassie Blue Staining Solution. After color development, the gels were removed from the stain and destained by washing with the Clearing Solution until protein bands were distinct.

Esterases

Esterase enzyme patterns were visualized in the 7½% Basic Acrylamide Gels and Acidic Acrylamide Gels by staining with a chromogenic substrate solution. The gel was placed in a dish and covered with Esterase Staining Solution until esterase bands were distinct.

Basic Gels Total Protein

As further identification, the basic gels total protein tube gels were run to show proteins rather than esterases with the Basic Acrylamide Gels. The tube gels were covered with Aniline Blue Black Staining Solution. After color development, the stain was poured off the gels and the gels were destained with 7.5% glacial acetic acid until protein bands were distinct.

Protein Patterns

A conventional numbering system is used for assigning locations to each soluble protein band and each esterase band visualized by the above procedures. (See Desborough, S. et al., *Am. Potato J.*, supra and Desborough, S. et al., *Phytochemistry*, 6, 989–994 (1967)). Using this numbering system, the electrophoretic patterns for FL1625 soluble proteins and esterases was determined to be as follows:

SM 1234 SL 33A467$^f$/8 EB 456$^2$ EA 2345

Figure 1E:
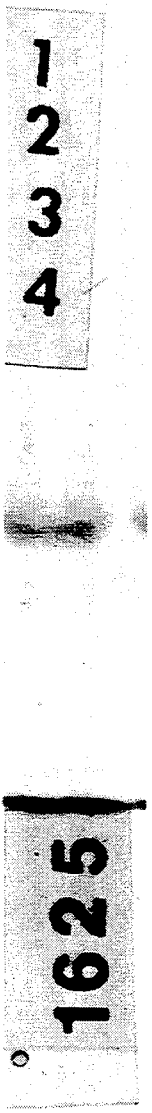
FIG. 1e is a photograph of the electrophoretic fingerprint pattern from basic gels total protein (BP) gels of potato cultivar FL1625.
Figure 1D:
FIG. 1d is a photograph of the electrophoretic fingerprint pattern from esterases in basic (EB) gels of potato cultivar FL1625.
Figure 1C:
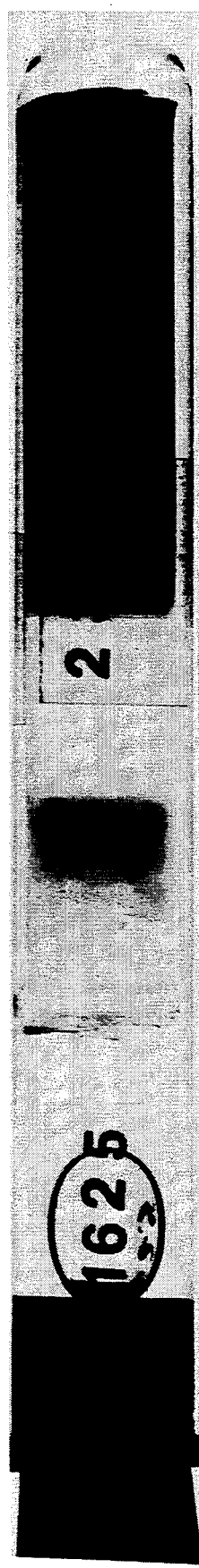
FIG. 1c is a photograph of the electrophoretic fingerprint pattern from esterases in acid (EA) gels of potato cultivar FL1625.
Figure 1B:
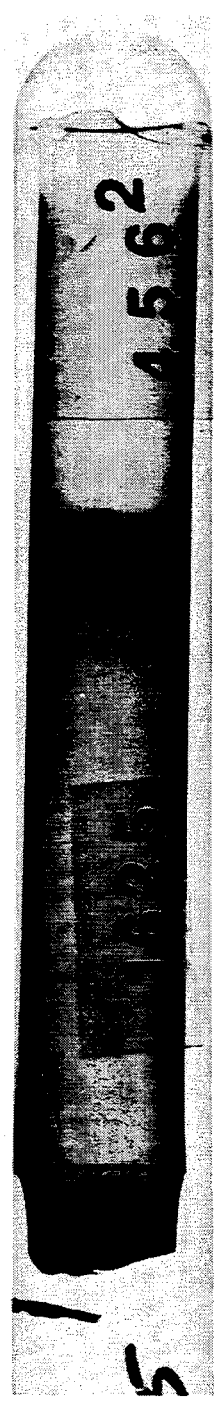
FIG. 1b is a phototgraph of the electrophoretic fingerprint pattern from the soluble protein lower bands (SL) of potato cultivar FL1625.
Figure 1A:
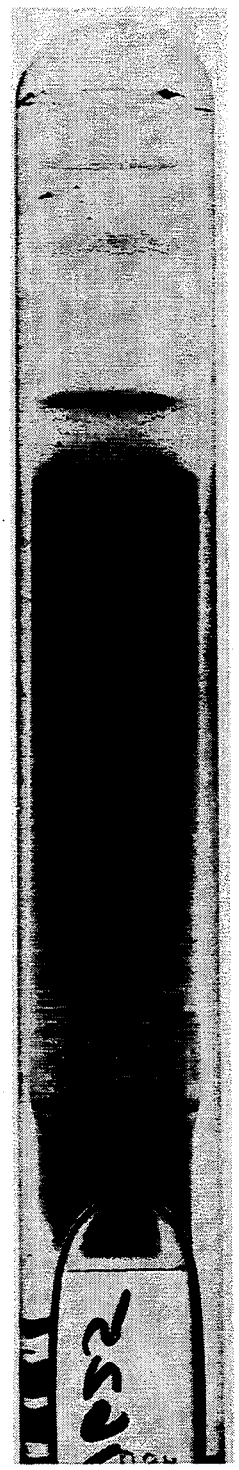
FIG. 1a is a photograph of the electrophoretic fingerprint pattern from the soluble protein middle bands (SM) gels of potato cultivar FL1625.

SM stands for soluble protein middle bands, SL stands for soluble protein lower bands, EB stands for esterases in basic gel bands, and EA stands for esterases in acid gel bands. BP stands for basic gels total protein. The SM bands were determined in 10% SDS gels while the SL bands were determined in 12.5% SDS gels. Superscript "c" indicates a concentrated band, superscript "f" indicates a faint band and numerical superscripts indicate multiple band (e.g., doublet or triplet) at the indicated location. Photographs of the soluble protein middle bands (SM), lower bands (SL), esterases in basic gels (EB), and esterases in acid gels (EA) electrophoresis gels of cultivar FL1625 are shown in FIGS. 1*a*, 1*b*, 1*c*, and 1*d* respectively. FIG. 1*e* shows a photograph of the basic gels total protein electrophoresisgel of cultivar FL1625.

I claim:

1. A potato cultivar of the genus and species *Solanum tuberosum*, Group Tuberosum, having moderately green foliage, vigorous vine growth and white flowers, having tubers characterized by a white flesh color and white tuber skin color, a relatively high specific gravity, a flattish round to blocky oval shape, and having the proteins which are indicated by the protein electrophoretic fingerprint pattern substantially as shown in FIGS. 1*a*, 1*b*, 1*c*, 1*d* and 1*e* of the drawings.

2. The potato cultivar of claim 1 wherein the tubers are generally flattish round in shape and have a length of from about 8.57 to about 12.06 cm, a width of from about 7.30 to about 9.52 cm, a thickness of from about 5.39 to about 8.25 cm, and specific gravity of from about 1.062 to about 1.107.

3. A potato cultivar, variety FL1625, a tissue culture of which is on deposit with the American Type Culture Collection, accession number 40316.

4. A tissue culture of *Solanum tuberosum*, having ATCC accession number 40316.

5. A potato plant regenerated from the tissue culture of claim 4.

* * * * *

UNITED STATES PATENT AND TRADEMARK OFFICE
CERTIFICATE OF CORRECTION

PATENT NO. : 5,434,342
DATED : July 18, 1995
INVENTOR(S) : Martin S. Cipar

It is certified that error appears in the above-indentified patent and that said Letters Patent is hereby corrected as shown below:

Col. 3, line 15, "(§)" should be --  --; Col. 5, line 59, "0.5g" should be -- 2.5g --; Col. 6, line 42, "$H_{20}$" should be -- $H_2O$ --; Col. 7, line 1, after "distilled" insert -- $H_2O$ --;
In the Claims: Col. 10, line 7 (claim 1), "blocky oval" should be -- blocky-oval --.

Signed and Sealed this

Fourteenth Day of November, 1995

Attest:

Bruce Lehman

BRUCE LEHMAN

Attesting Officer        Commissioner of Patents and Trademarks